US011596351B2

(12) United States Patent
Nair (10) Patent No.: US 11,596,351 B2
(45) Date of Patent: Mar. 7, 2023

(54) DEVICES, SYSTEMS, AND METHOD FOR NON-INVASIVE TISSUE CHARACTERIZATION

(71) Applicant: PHILIPS IMAGE GUIDED THERAPY CORPORATION, San Diego, CA (US)

(72) Inventor: Anuja Nair, Bedford, MA (US)

(73) Assignee: PHILIPS IMAGE GUIDED THERAPY CORPORATION, San Diego (GA)

( * ) Notice: Subject to any disclaimer, the term of this patent is extended or adjusted under 35 U.S.C. 154(b) by 0 days.

(21) Appl. No.: 16/859,668

(22) Filed: Apr. 27, 2020

(65) Prior Publication Data

US 2020/0253550 A1 Aug. 13, 2020

Related U.S. Application Data

(63) Continuation of application No. 14/096,960, filed on Dec. 4, 2013, now Pat. No. 10,631,780.

(60) Provisional application No. 61/733,738, filed on Dec. 5, 2012.

(51) Int. Cl.
*A61B 5/00* (2006.01)
*A61B 8/08* (2006.01)
*A61B 8/00* (2006.01)

(52) U.S. Cl.
CPC .......... *A61B 5/4869* (2013.01); *A61B 8/5207* (2013.01); *A61B 8/5223* (2013.01); *A61B 5/441* (2013.01); *A61B 8/0858* (2013.01); *A61B 8/0891* (2013.01); *A61B 8/4416* (2013.01); *A61B 8/4472* (2013.01)

(58) Field of Classification Search
None
See application file for complete search history.

(56) References Cited

U.S. PATENT DOCUMENTS

| 6,200,268 B1 | 3/2001 | Vince |
| 6,301,378 B1 * | 10/2001 | Karssemeijer ....... G06K 9/4604 378/37 |
| 6,381,350 B1 | 4/2002 | Klingensmith |
| | (Continued) | |

OTHER PUBLICATIONS

Hoffman et al, "Layer-Dependent Variation in the Anisotropy of Apparent Integrated backscatter from human Coronary Arteries", Ultrasound in Medicine and Biology, vol. 37, No. 4, pp. 632-641, Nov. 2011.

*Primary Examiner* — Amelie R Davis
*Assistant Examiner* — Marjan Saboktakin (57) ABSTRACT

Disclosed herein is a non-invasive system for determining tissue composition. The system comprises an imaging system with a non-invasive probe, a signal analyzer, and a correlation processor. The probe includes active imaging components for emitting energy and collecting imaging data including reflected signals from an object of interest. The signal analyzer analyzes the imaging data and determines one or more signal properties from the reflected signals. The correlation processor then associates the one or more signal properties to pre-determined tissue signal properties of different tissue components through a pattern recognition technique wherein the pre-determined tissue signal properties are embodied in a database, and identifies a tissue component of the object based on the pattern recognition technique.

16 Claims, 8 Drawing Sheets

(56) References Cited

U.S. PATENT DOCUMENTS

| | | | |
|---|---|---|---|
| 6,837,853 B2 | 1/2005 | Marian | |
| 7,672,491 B2 | 3/2010 | Krishnan | |
| 2004/0152983 A1* | 8/2004 | Vince | A61B 8/00 600/454 |
| 2005/0049497 A1 | 3/2005 | Krishnan | |
| 2008/0075348 A1* | 3/2008 | Rappaport | G06K 9/6255 382/132 |
| 2009/0306509 A1* | 12/2009 | Pedersen | A61B 8/4254 600/446 |
| 2009/0318815 A1 | 12/2009 | Barnes | |
| 2011/0125025 A1 | 5/2011 | Hart | |
| 2011/0150310 A1* | 6/2011 | Endo | G06T 7/32 382/131 |

\* cited by examiner

DEVICES, SYSTEMS, AND METHOD FOR NON-INVASIVE TISSUE CHARACTERIZATION

CROSS-REFERENCE TO RELATED APPLICATIONS

The present application is a continuation of U.S. application Ser. No. 14/096,960, filed Dec. 4, 2013, now U.S. Pat. No. 10,631,780, which claims priority to and the benefit of U.S. Provisional Patent Application No. 61/733,738, filed Dec. 5, 2012, each of which is hereby incorporated by reference in its entirety.

BACKGROUND

Imaging various tissues and organs of the human body provides useful information in various disciplines of medical practice for determining the best type and course of treatment. For example, intravascular imaging technologies have enabled doctors to create and view a variety of images generated by an imaging device inserted within vasculature. Imaging of the coronary vessels of a patient by techniques involving intravascular insertion of a catheter-mounted probe (e.g., an ultrasound transducer array) can provide physicians with valuable information. Such image data indicates the extent of a stenosis in a patient, reveals progression of disease, and helps determine whether procedures such as angioplasty or atherectomy are indicated or whether more invasive procedures are warranted.

The development of new imaging and/or examining technologies has provided an increasing number of options available to doctors for the non-invasive diagnosis and evaluation of disease. Medical technologies for externally imaging and/or examining both external and internal bodily structures offers a diagnostic tool to establish the need for treatment of a diseased structure, to determine the most appropriate course of treatment, and to assess the effectiveness of the treatment. Such external imaging and/or evaluation techniques can complement traditional radiological imaging techniques (e.g., angiography and mammography) by providing images of the tissue and/or fluid flow without introducing instruments (and the associated health risks) into the patient's body. Internal body structures may be imaged and/or examined to determine the structural or flow characteristics that may indicate abnormalities such as, but not limited to, tumors, cysts, abscesses, mineral deposits, obstructions, plaques, and other anatomical defects or pathologies. Often these high quality images are generated in substantially real time. However, analysis of these images often localizes the object of interest but does not characterize the tissue, requiring a biopsy to classify the tissue and establish a definitive diagnosis. Also, analysis of these images are dependent upon highly trained observers and may be subject to observer biases and result in known observer-variability.

The devices, systems, and methods disclosed herein overcome one or more of the deficiencies of the prior art.

SUMMARY

The present disclosure provides devices, systems, and methods for determining the type(s) of tissue present within a patient utilizing a non-invasive, external imaging probe. The resulting determination of the tissue type(s) can be utilized to determine an appropriate, customized treatment plan for the patient, leading to improved patient outcomes.

The present disclosure relates generally to non-invasive tissue characterization within an animal, including human bodies. In one aspect, the present disclosure provides a system for determining tissue composition based on signals received from a non-invasive probe. The system includes a signal analyzer for analyzing the imaging data and determining one or more signal properties from the reflected signals along with a correlation processor configured to associate the one or more signal properties to pre-determined tissue signal properties of different tissue components through a pattern recognition technique. The pre-determined tissue signal properties can be embodied in a database, and the correlation processor is further configured to identify a tissue component based on the pattern recognition technique. In one alternative form, the imaging system collects imaging data from more than one imaging modality, and the signal analyzer is configured to analyze more than one type of imaging data to determine signal properties associated with each imaging modality. In this alternative form, the correlation processor is configured to identify a tissue component of the object based on associating the signal properties to pre-determined tissue signal properties of different tissue components for the different imaging modalities.

In another aspect, the disclosure provides an article of manufacture embodied in a computer-readable medium for use in a processing system for analyzing imaging signal data associated with a non-invasive imaging probe. The article of manufacture comprising first processor executable instructions for causing a processor to receive imaging signal data of a scanned object collected from a non-invasive probe; second processor executable instructions for causing the processor to determine signal properties of one or more regions of interest associated with the scanned object from the image signal data; and third processor executable instructions for causing the processor to classify the one or more regions of interest as a tissue component type based on a classification data structure pre-determined from measured associations between signal properties, secondary parameters, and one or more tissue component types of an object similar to the scanned object.

In still a further aspect, the present disclosure provides a method of identifying one or more tissue components of a scanned object of a patient. The method comprising receiving reflected signals from a non-invasive probe scanning the object from a location external to the object; determining one or more signal properties from the reflected signals; associating the one or more signal properties to pre-determined signal properties of tissue components of an object similar to the scanned object wherein the pre-determined signal properties comprise classification conditions stored in a data structure; and identifying one or more tissue components based on the associating.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure. Throughout this description, like elements, in whatever embodiment described, refer to common elements wherever referred to and referenced by the same reference number. The characteristics, attributes, functions, interrelations ascribed to a particular element in one location apply to those elements when referred to by the same reference number in another location unless specifically stated otherwise.

The figures referenced below are drawn for ease of explanation of the basic teachings of the present disclosure only; the extensions of the figures with respect to number, position, relationship and dimensions of the parts to form the preferred embodiment will be explained or will be within the skill of the art after the following description has been read and understood. Further, the exact dimensions and dimensional proportions to conform to specific force, weight, strength and similar requirements will likewise be within the skill of the art after the following description has been read and understood.

The following is a brief description of each figure used to describe the present invention, and thus, is being presented for illustrative purposes only and should not be limitative of the scope of the present invention.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure describes systems and methods for tissue characterization by analyzing images created by an energy emission device, such as, by way of non-limiting example, an ultrasound transducer, deployable with an imaging system to facilitate interpretation of images of a patient's tissues of interest, such as a blood vessel or tumor. The systems and methods described herein correlate image properties of the tissues of interest with pre-determined tissue properties to automatically and reproducibly characterize the tissues of interest in real time (i.e., as the tissues are being imaged). In some embodiments, the systems and methods described herein utilize various parameters related to the angle of incidence of the imaging modality, particular anatomical characteristics of the patient, and/or medical conditions of the patient to better characterize the tissues of interest. In particular, the disclosure describes one embodiment that performs tissue characterization of an intravascular plaque using images obtained using an external ultrasonic device. By automatically and reproducibly characterizing the imaged tissues in real time, the systems and methods described herein minimize the known observer-variability associated with tissue characterization by observers. Moreover, by specifically characterizing tissue types, the systems and methods described herein reduce the need for post-imaging biopsies before initiating treatment, thereby accelerating the onset of treatment for the patient.

It should be appreciated that while the exemplary embodiment is described in terms of an ultrasonic device, or more particularly the use of ultrasound data (or a transformation thereof) to render images of a bodily structure or object, the present disclosure is not so limited. Thus, for example, using backscattered data (or a transformation thereof) based on spectroscopy or even electromagnetic radiation (e.g., light waves in non-visible ranges such as used in OCT, X-Ray CT, etc.) to render images and/or imaging data of any tissue type or composition (not limited to vasculature, but including other structures both within and on the surface of a patient, including human as well as non-human patients) is within the spirit and scope of the present disclosure. Any form of external imaging, measuring, and/or evaluation device (and resultant data) is within the spirit and scope of the present disclosure.

The following includes definitions of selected terms used throughout the disclosure. Both singular and plural forms of all terms fall within each meaning.

"Computer-readable medium," as used herein, refers to any medium that participates in directly or indirectly providing signals, instructions and/or data to one or more processors for execution. Such a medium may take many forms, including but not limited to, non-volatile media, volatile media, and transmission media. Non-volatile media may include, for example, optical or magnetic disks. Volatile media may include dynamic memory. Transmission media may include coaxial cables, copper wire, and fiber optic cables. Transmission media can also take the form of acoustic or light waves, such as those generated during radio-wave and infra-red data communications, or take the form of one or more groups of signals. Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, a PROM, an EPROM, a FLASH-EPROM, any other memory chip or cartridge, a carrier wave/pulse, or any other medium from which a computer, processor or other electronic device can read.

"Logic," as used herein, includes, but is not limited to, hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), a programmed logic device, memory device containing instructions, or the like. Logic may also be fully embodied as software.

"Patient," as used herein, includes, but is not limited to, a living animal including humans and non-humans.

"Signal," as used herein, includes, but is not limited to, one or more electrical signals, analog or digital signals, one or more computer or processor instructions, messages, a bit or bit stream, or other means that can be received, transmitted, and/or detected.

"Software," as used herein, includes, but is not limited to, one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in memory, part of an operating system or other type of executable instructions. It will be appreciated by one of ordinary skill in the art that the form of software is dependent on, for example, requirements of a desired application, the environment it runs on, and/or the desires of a designer/programmer or the like.

"User," as used herein, includes, but is not limited to, one or more persons, software, computers or other devices, or combinations of these.

Figure 1:
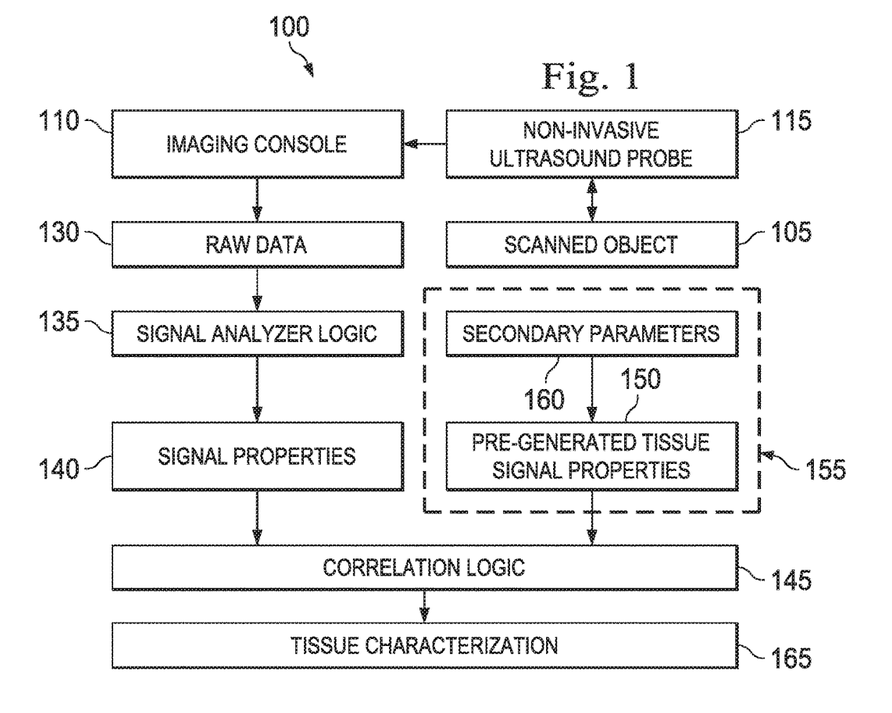
FIG. 1 is a simplified block diagram of the individual components of an exemplary external imaging system, including a probe, according to one embodiment of the present disclosure.

With reference to the figures, FIG. 1 illustrates one embodiment of a tissue characterization system 100 configured to non-invasively scan an object 105 and analyze one or more characteristics of the object 105, which may be located on the external surface or inside a patient's body. In the pictured embodiment, the system 100 includes an imaging system console 110 that includes data processing, analysis, and/or display capabilities. The imaging console 110 may be a general purpose computer configured to communicate with and collect data from an imaging probe 115. In another embodiment, the imaging console 110 may be, for example, a General Electric Vivid 5 Echocardiography System, a Hewlett-Packard SONOS System, or other types of ultrasound systems. In another embodiment, the console 110 may be a small portable scanner. In the pictured embodiment, the imaging probe 115 is a non-invasive device configured to scan the object 105 from a location external to a patient's body. As used herein, the term "non-invasive" refers to procedures in which no break in the skin surface is created. As such, the term "non-invasive" encompasses procedures extending through natural body orifices, such as, by way of non-limiting example, the mouth, the nasal cavity, the ear canal, esophagus, or the rectum. Various types of probes can be used, such as, by way of non-limiting example, a phased-array ultrasound probe, an OCT probe, a spectroscopy probe, a multi-modality or combination probe (incorporating various imaging modalities), a linear probe, a curvilinear probe, or other types of hand-held probes.

Figure 2A:
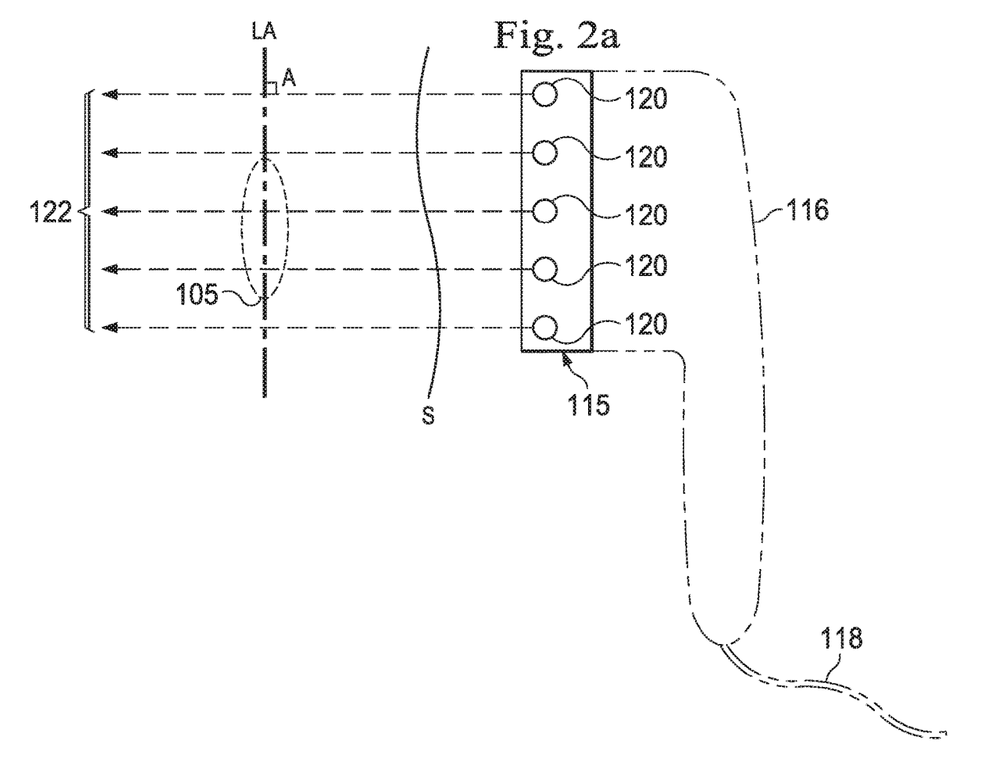
FIGS. 2a and 2b are illustrations of an imaging probe (a) scanning an object and (b) receiving reflected signals from the object according to one embodiment of the present disclosure.

As shown in FIG. 2a, to perform a scan, the probe 115 may be placed against or near the patient's skin S near the object or region of interest 105. The non-invasive probe 115 is shaped and configured for use against and/or near the external skin surface S of a patient. In that regard, the shape and configuration of the probe 115 illustrated herein is for exemplary purposes only and in no way limits the manner in which the probe 115 may be shaped in other embodiments. The probe can include a housing 116 adapted for gripping by a user and have a communication connection 118 to a console (not shown). Alternatively, the communication connection can be a wireless connection. Generally, the probe 115 may be configured to take on any desired profile, which may depend upon the type of imaging probe (e.g., ultrasound, OCT, multi-modality, etc.), the desired application, or the particular tissue of interest. In some embodiments, aspects of the probe 115 may be substantially similar to aspects of an ultrasound probe disclosed in U.S. Pat. No. 6,837,853, titled "System and Method for Using an Ultrasound Transducer with an Integrated Transducer Information System," which is incorporated by reference herein in its entirety. In some embodiments, aspects of the probe 115 may be substantially similar to aspects of an ultrasonic probe disclosed in U.S. Patent Application No. 2011/0125025, titled "Three Dimensional Imaging Ultrasound Probe," which is incorporated by reference herein in its entirety.

The active imaging components 120 (e.g., the transducers of an ultrasound probe) of the probe 115 can be activated along different paths or scan lines 122 directed at the object or region of interest and emit energy along those paths. Although the active imaging components 120 are arranged linearly so as to create a parallel array of paths 122 in the pictured embodiment, in other embodiments, the active imaging components may be positioned on the probe 115 in any of a variety of arrangements. Thus, in other embodiments, the active imaging components may be arranged so as to create a nonparallel array of energy emission paths. In the pictured embodiment, the imaging probe 115 is positioned substantially parallel to a longitudinal axis LA of the object, such that the emitted energy contacts the object 105 at an angle of incidence A that is substantially ninety degrees relative to the longitudinal axis LA of the object 105. In other embodiments, as indicated below in FIGS. 3a-3c, the imaging probe may be positioned at any of a variety of angles relative to the object 105 so as to enable the emitted energy to interact with the object 105 at a variety of angles of incidence A.

Figure 3A:
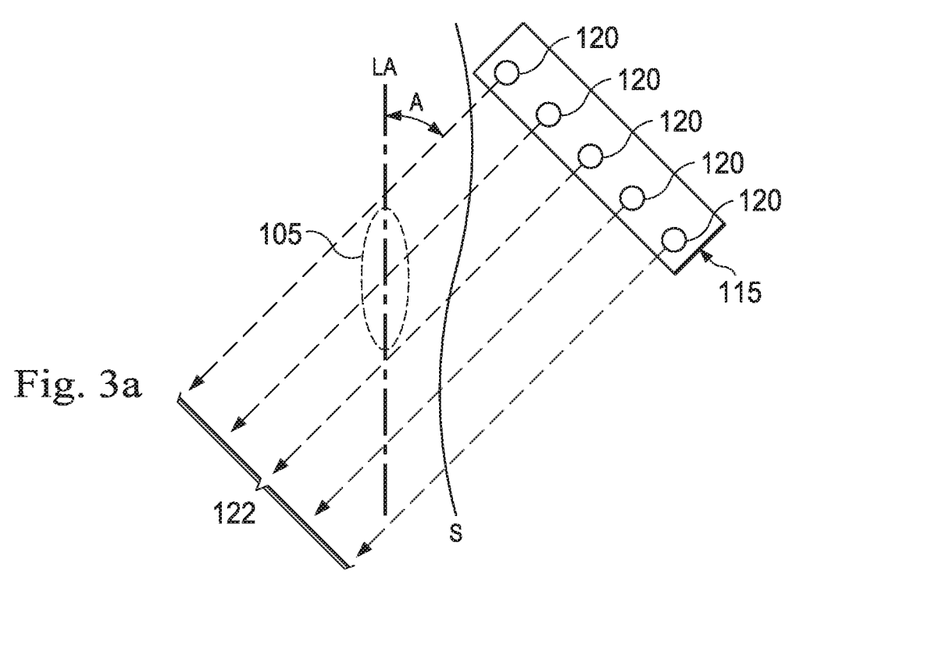
FIGS. 3a-3d are illustrations of an imaging probe scanning an object at different angles of incidence relative to the object according to one embodiment of the present disclosure.
Figure 3B:
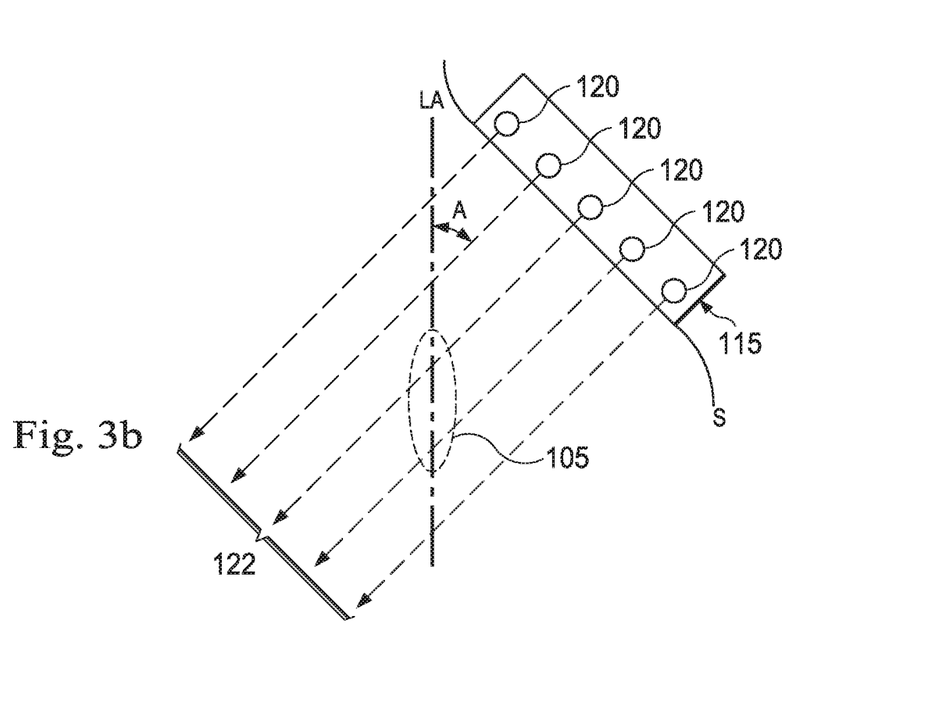
Figure 3C:
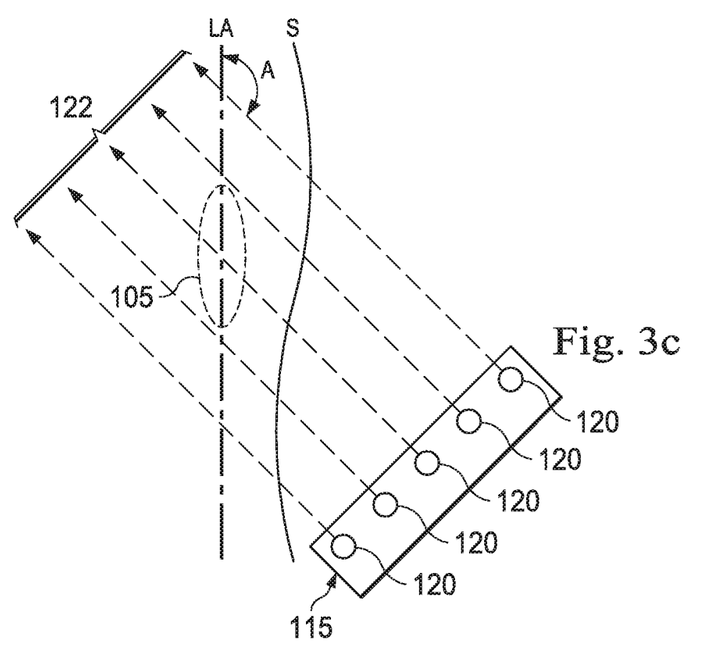
Figure 3D:
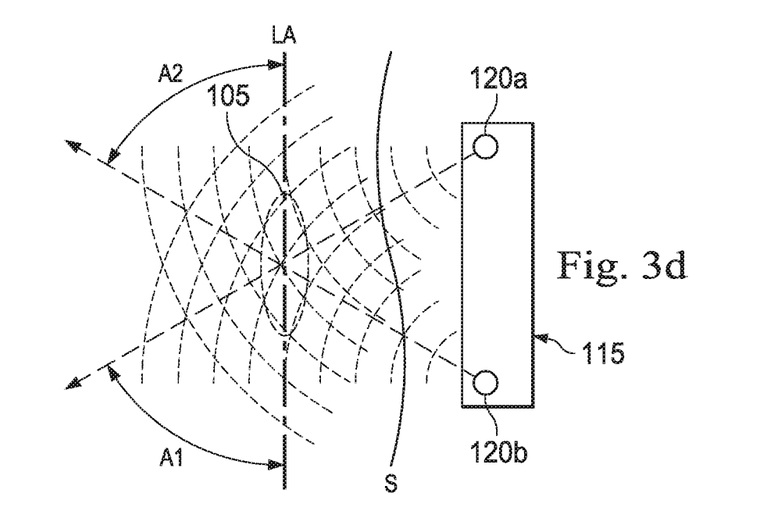

In some embodiments, as shown in FIG. 3d, the active imaging components 120 may emit energy at a variety of angles of incidence A although the imaging probe 115 itself remains positioned relatively parallel to the longitudinal axis LA of the object 105. In FIG. 3d, the active imaging component 120a emits energy (e.g., ultrasound waves) toward the object 105 at an angle of incidence A1, and the active imaging component 120b emits energy at an angle of incidence A2. In one embodiment, the energy emitted by different active imaging components intersects and simultaneously interact with the object 105, resulting in a characteristic pattern of reflected energy. In one aspect, non-parallel emitters may be activated substantially simultaneously. In one aspect, non-parallel emitters may be activated sequentially. In another aspect, non-parallel emitters operate at different frequencies.

Figure 2B:
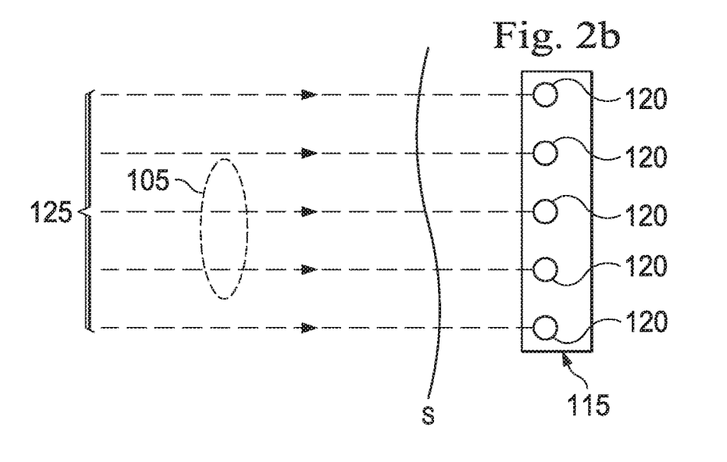

As shown in FIG. 2b, the active imaging components 120 then acquire data reflected from the tissue along each path 122. Different types and densities of tissue absorb and reflect emitted energy differently. Tissues that receive the emitted energy reflect and transmit some of the energy as reflected signals 125. The reflected signals 125 are then received by the active imaging components 120 in the probe 115. The reflected signals 125 are shown as parallel signals for illustrative purposes only. In actuality, the reflected signals 125 may approach to the probe 115 at any of a variety of angles. In some embodiments, the active imaging components comprise combined energy emitting and energy receiving components (i.e., individual components capable of performing both functions). In other embodiments, the active imaging components comprise separate energy emitting and energy receiving components. The difference between the energy signals transmitted and received by the probe 115 is that the received signal 125 is the attenuated (and possibly backscattered) version of the transmitted signal.

Each reflected signal 125 is characteristic of the type of tissues that reflected it. Differences in the reflected signal 125 along each path can be determined by performing analysis on the signals. As a result, identifying different signal characteristics along each path 122 allows for a correlation to the type of tissue associated with those particular signal characteristics. As will be described below, the signal characteristics of each reflected signal 125 can serve as a signature for different types of components within the object 118, including, for example, plaque components within an artery or malignant cell types within a tumor.

FIGS. 3a-3d illustrate the non-invasive imaging probe 115 scanning the object 105 at different angles of incidence relative to the longitudinal axis LA of the object 105 according to one embodiment of the present disclosure. In FIG. 3a, the probe 115 is positioned at an angle above the skin surface S, and the emitted energy interacts with the object 105 at an acute angle of incidence A (relative to the longitudinal axis LA of the object 105). In FIG. 3b, the probe 115 is positioned pushing against the skin surface S at an angle relative to the object 105, and the emitted energy interacts with the object 105 at an acute angle of incidence A (relative to the longitudinal axis LA of the object 105). In FIG. 3c, the probe 115 is positioned at an angle above the skin surface S, and the emitted energy interacts with the object 105 at an obtuse angle of incidence A (relative to the longitudinal axis LA of the object 105).

The reflective signals 125 obtained from the object 105 will typically be characteristic of the angle of incidence A of the emitted energy. For example, a series of reflective signal data sets obtained at different angles of incidence can help distinguish between isotropic and anisotropic tissues. For example, isotropic tissues (e.g., fat) typically have identical properties in all directions, while anisotropic tissues (e.g., muscle fibers) have directionally dependent properties. In some instances, different types of tumors and mass lesions may have characteristic anisotropic properties. Isotropic and anisotropic tissues have different acoustic and/or optical impedances and properties when the source of the imaging signals are orthogonal or at other angles to the tissue. For example, if all the data sets of reflected signals from the object 105 reveal the same information, regardless of the angle of incidence associated with each set, the imaging system 100 may be alerted to the presence of isotropic tissue. In contrast, if the data sets of reflected signals from the object 105 reveal different information, the imaging system 100 may be alerted to the presence of anisotropic tissue (and, in some instances, a particular type of anisotropic tissue). In some instances, the user may reposition the probe 115 at a series of different angles around the object 105 so as to obtain a series of sets of reflective signals 125, wherein each set is associated with a different angle of incidence A relative to the object 105. In some instances, such as where the active imaging components 120 of the probe 115 are moveable or otherwise capable of emitting energy at a variety of angles, the user may obtain such a series of sets of reflective signals 125 without repositioning the probe 115.

Referencing FIG. 1, the data collected by the probe 115 is initially in the form of raw data 130 of the reflected signals 125 along each scan line. The data 130 is then refined or transformed into a format that can be analyzed to determine various signal characteristics that may identify associated tissue types within and adjacent to the scanned object 105. A signal analyzer logic 135 is configured to process and analyze the data 130 to identify, in real-time, the various components of the scanned object 105. The logic 135 is configured to identify various types of tissue and/or cells and to provide an assessment as to the patient's condition based on the type of tissues and/or cells identified, an amount of tissue and/or cells identified, or both.

The signal analyzer logic 135 includes logic to transform the data 130 into an analyzable domain and analyze the transformed information from the signals to determine one or more signal properties 140. For example, each scan line can be analyzed in segments and signal properties can be determined for each segment. The segments may be equal in size, different in size, equally spaced from each other, overlapping each other, and/or defined in other desired ways.

The signal properties 140 are processed by correlation logic 145 configured to correlate the signal properties of the scan line segment with the type of tissue component having those or similar signal properties. In that regard, the correlation logic 145 is configured to compare and match the signal properties 140 to pre-determined or pre-generated tissue signal properties 150 contained within a database 155. Various parameters may comprise the database of pre-determined tissue signal properties 150. The parameters comprising the database 155 would be pertinent to both the desired application or tissue-of-interest and the imaging modality of the imaging probe (i.e., ultrasound, OCT, spectroscopy, etc.). In addition, the database can contain other information or 'macro' data. These could be: (a) patient demographics related (age, gender, race) or (b) patient health-specific (diabetes, history of hypertension, arthritis, or other related criteria depending on the tissue being evaluated), or (c) more related to the tissue being evaluated (size and location of lesion in the coronary tree—close to a bifurcation or not, restricting blood flow or not, etc.). The correlation logic 145 is configured to recognize the type of imaging modality employed by the imaging probe 115 and to use the appropriate pre-determined tissue signal properties 150 associated with that particular imaging modality. For example, if the imaging modality being used were ultrasound, the pre-determined signal properties 150 may include various parameters in the spectral domain directly associated with scatter size, density, viscosity, and their acoustic properties such as impedance and attenuation coefficient.

In some embodiments, the imaging system 100 may employ a multitude of different imaging modalities to image the same object 105. In some embodiments, these imaging modalities are used sequentially, whereas in other embodiments, the different imaging modalities are used simultaneously (e.g., using a multi-modality imaging probe 115). In one embodiment, the imaging probe 115 may be configured to image the object 105 using a multitude of different imaging modalities (e.g., OCT and ultrasound). In some embodiments, the correlation logic 145 is configured to combine or analyze the pre-determined signal properties 150 associated with each imaging modality used to perform the tissue characterization 165.

Secondary parameters 160 may be included within the data structure to reflect the non-invasive nature of the imaging and/or the particular pre-existing conditions or differential diagnoses of the patient. The secondary parameters 160 may be utilized by the correlation logic to more accurately compare and match the signal properties 140 to the pre-determined signal properties 150. One secondary parameter 160 associated with the non-invasive nature of the imaging may comprise the patient's body-mass index to give an indication of the amount of muscle, fat, and other tissue that may lie in the path of the energy emitted by the probe, which may affect the attenuation of the energy emitted toward and reflected from the object or region of interest.

Another secondary parameter 160 associated with the non-invasive nature of the imaging may comprise the angle of incidence of the imaging probe (or, more precisely, the emitted energy) relative to the object 105. In some embodiments, the imaging system 100 can determine the angle of incidence A of the emitted energy relative to the longitudinal axis LA of the object 105 and use this as a secondary parameter before automatically selecting the appropriate pre-determined signal properties associated with that angle of incidence or appropriately adjusting the pre-determined signal properties 150 to reflect this angle of incidence. In other embodiments, the user may enter the angle of incidence A manually (e.g., via a graphical user interface attached to the imaging console 110), and either the user or the imaging system 100 may select the appropriate pre-determined signal properties 150 associated with that angle of incidence or appropriately adjust the pre-determined signal properties to reflect this angle of incidence. In some embodiments, a three-dimensional data set can be constructed with the imaging probe 115 to provide further parameters related to tissue isotropy and/or anisotropy and matched back to the secondary parameters 160 in the database 155 that contains these pre-determined values at various angles of incidence.

Another secondary parameter 160 associated with the imaging may comprise the particular frequency or harmonics employed by the imaging probe 115. For example, the database 155 may contain particular sets of pre-determined signal properties 150 associated with particular frequencies or harmonic patterns.

Other secondary parameters 160 included within the database of pre-determined signal properties may relate to the particular pre-existing conditions or differential diagnoses of the patient. For example, in the context of imaging atherosclerosis non-invasively, it might be important to relate whether a patient is diabetic and/or hypertensive to better analyze the signal properties and to give an appropriate disease risk level. The secondary parameters 160 may be entered into the database 155 by the user or be selected from a pre-established menu or list of options already present within the database.

In one embodiment, the pre-determined signal properties 150 and secondary parameters 160 discussed above are configured in the database 155 or data structure that associates measured or observed signal properties 140 to pre-determined tissue signal properties 150 that reflect specific types of tissue component such as, by way of non-limiting example, fluid, blood, normal tissue, necrotic tissue, benign tumor tissue, or malignant tumor tissue. The data structure 155 may be implemented in a variety of ways including a data file, an array, a table, a linked list, a tree structure, a database, neural network, combinations of these and multiple components of each if desired. The correlation logic 145 matches the signal properties 140 from a path or scan line, or a region of the path or scan line, to the pre-determined properties 150 and outputs a tissue characterization 165 that identifies the type of tissue (and/or cell). In some embodiments, the correlation logic 145 weights the pre-determined properties with other parameters (such as body-mass index) before matching the signal properties 140 from a path or scan line, or a region of the path or scan line, to the weighted pre-determined properties 150 and outputting a tissue characterization 165. The system 100 then repeats the analysis for other segments on the current path or scan line and then for the other paths or scan lines. The analysis can be performed along a single path in one dimension, multiple paths within the same plane can be analyzed for two dimensional considerations, or a series of scans forming a three dimensional volume can be analyzed. In some embodiments, the system 100 may repeat the analysis for the imaging data received by each of the other imaging modalities. In some such embodiments, the system 100 utilizes the correlation logic 145 to combine the correlation conclusions from different imaging modalities to arrive at a final tissue characterization 165.

Figure 4:
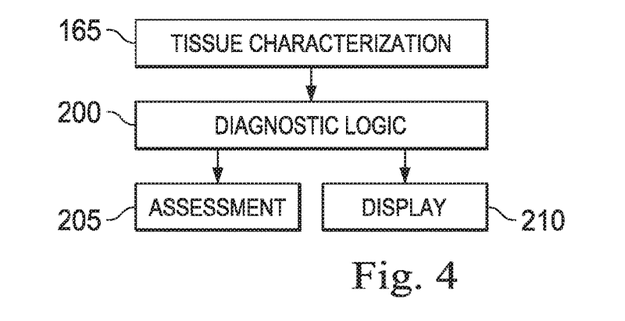
FIG. 4 is a simplified block diagram of individual components of an exemplary external imaging system according to one embodiment of the present disclosure.

With reference to FIG. 4, once a sufficient amount of data is analyzed and the tissue types of the object 105 are characterized, a diagnostic logic 200 may be included in the imaging system 100 to generate an assessment 205 as to the type and amount of different tissues identified and a health condition of the patient in light of the patient's preexisting health conditions, symptoms, and differential diagnosis. Additionally, the diagnostic logic 200 may be configured to reconstruct the received data into displayed images, and the identified components may be visually distinguished on a display 210. In some embodiments, the display 210 may be included as a component of the imaging console 110 (shown in FIG. 1). In other embodiments, the display 210 may be an independently located device that communicates either wirelessly or through a wired connection with the imaging system 100. In some embodiments, the display 210 may be remotely located.

Based on the assessment of the scanned object or region of interest, the diagnostic logic 200 can be configured to generate a score indicating the health condition of a patient. For example, in one instance, if the scanned object of interest was a mass, a score of zero may indicate no risk of malignancy while a score of ten may indicate a high risk of malignancy. With this score, a physician may recommend a particular treatment which may include monitoring, lifestyle changes, medication, radiation, and/or surgery. The score may also be helpful to convince a patient of the existence and gravity of their condition.

In one example, the imaging system 100 is configured to analyze ultrasound data collected from a scan of a carotid artery. In the example shown in FIG. 5, the imaging system includes component parts that are substantially similar to the component parts of the imaging system 100 shown in FIG. 1, except as otherwise described herein. The imaging console 500 comprises an ultrasound imaging console and the imaging probe 505 comprises an ultrasound probe, which includes one or more transducers 510 that acquire radio frequency data from the scanned object 515, or carotid artery. The carotid arteries comprise a pair of arteries that pass up through a patient's neck and supply blood to the head. By identifying and characterizing plaques from carotid ultrasound data, an assessment can be made as to a patient's risk of stroke or heart attack without an invasive procedure. The epidemiologic finding that cardiovascular and cerebrovascular morbidity are well correlated has led to the recognition of possible surrogates for the costly and sometimes invasive evaluation of the coronary circulation. An example of this is the Intima-Media Thickness (IMT) measurement, which is a recognized non-invasive means of assessing subclinical atherosclerosis.

Figure 5:
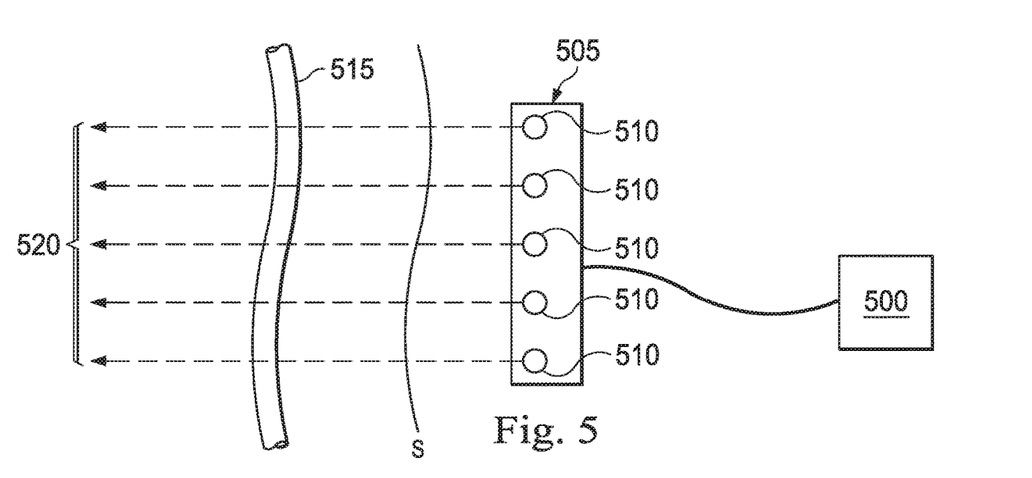
FIG. 5 is an illustration of an ultrasound probe scanning an object according to one embodiment of the present disclosure.

Illustrated in FIG. 5 is a simplified diagram of one embodiment of the ultrasound probe 505 including a linear array of the transducers 510. Depending on the type of probe, different numbers of transducers may be used, for example, 192 transducers. The transducers 510 may pulse separately, or together creating a plurality of the scan lines 520. By placing the probe 505 near or against a patient's neck, ultrasound data can be collected from the carotid artery 515.

To perform a scan, the ultrasound probe 505 would be placed near or against the skin surface S of a patient's neck near the carotid artery of interest 515. The transducers 510 of the probe would be pulsed along scan lines 520 and then acquire echoes of backscatter signals 525 (not shown) reflected from the tissue along each scan line. Different types and densities of tissue absorb and reflect the ultrasound pulses differently. Tissues that receive the pulsed signal reflect and transmit some of the pulse energy as a backscatter or reflected signal. The backscattered signals 525 are then received by the transducers 510 in the probe 505. The difference between the signals transmitted and received by the probe 505 is that the received signal 525 is the attenuated and backscattered version of the transmitted signal 520. This backscatter signal 525 is characteristic of the type of tissue that reflected it. Differences in the backscatter signal 525 along each scan line 520 can be determined by performing a frequency analysis, using spectral analysis and autoregressive coefficients, a wavelet decomposition, and/or a curvelet decomposition on the signals. As a result, identifying different signal characteristics along each scan line allows for a correlation to the type of tissue associated with those particular signal characteristics. As described above, signal characteristics of the backscattered signal 525 can serve as a signature for different types of components within an object, including, for example, plaque components within an artery.

With reference again to FIG. 1, the data collected by the ultrasound probe 505 is initially in the form of raw radio frequency (RF) data 130 of the backscattered signals along each scan line. The RF data 130 is then analyzed to determine various signal characteristics that may identify associated tissue types. The signal analyzer logic 135 is configured to process and analyze the radio frequency data 130 to identify, in real-time, the vascular components of the scanned carotid artery. Because different types and densities of tissue absorb and reflect the ultrasound pulses differently, the signal analyzer logic 135 utilizes the reflected backscatter data 130 transmitted back to the probe 505 to assemble a two-dimensional ultrasound characterization of a blood vessel from hundreds of pulse/acquisition cycles. In this embodiment, the logic is configured to identify various types of plaque components and to provide an assessment as to the patient's condition based on the type of plaque identified, an amount of plaque component identified, or both.

In one embodiment, the signal analyzer logic 135 includes logic to transform the RF data 130 to the frequency domain and analyze frequency information of the signals to determine one or more signal properties 140. For example, each scan line can be analyzed in segments and signal properties are determined for each segment. The segments may be equal in size, different in size, equally spaced from each other, overlapping each other, and/or defined in other desired ways.

Figure 6:
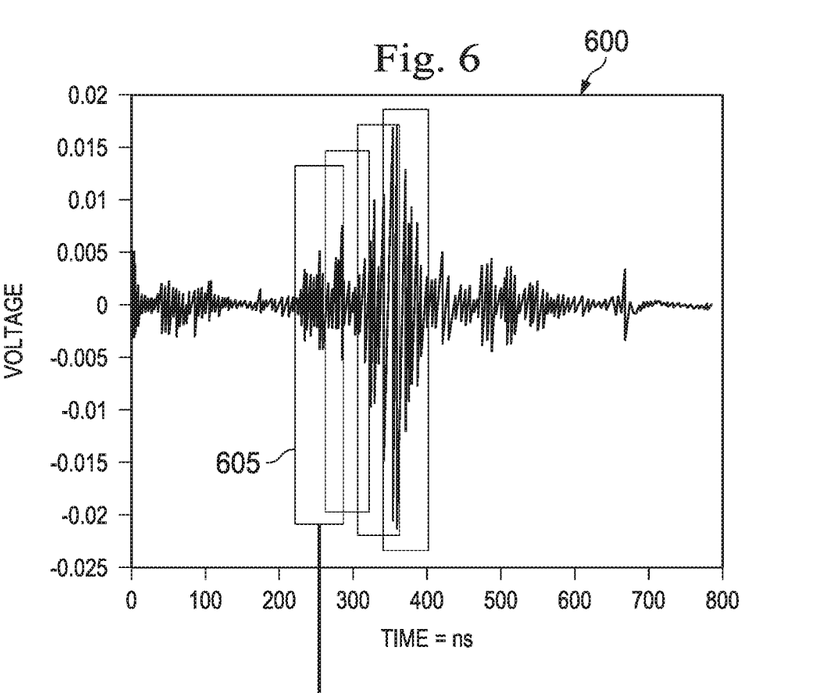
FIG. 6 is an illustration of an ultrasonic A-scan according to one embodiment of the present disclosure.
Figure 7:
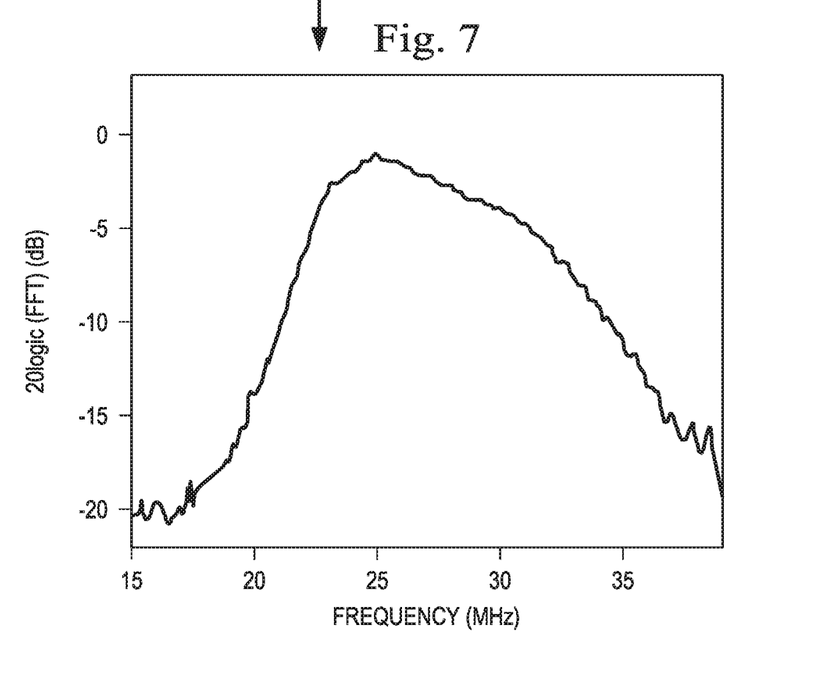
FIG. 7 is an illustration of a power spectrum plot generated from the A-scan signal shown in FIG. 6.

Illustrated in FIG. 6 is one example of RF data of one scan line 600 plotted as voltage over time. The scan line can be analyzed in segments represented by the windows illustrated in the figure, such as window 605. The RF data within the window 605 is transformed in this embodiment to a power spectrum density plot as shown in FIG. 7. Signal properties from the segment 605 are determined from the power spectrum of FIG. 7. Signal properties, in this case also referred to as spectral properties, may include the y-intercept, maximum power, mid-band fit, minimum power, frequencies at maximum and minimum powers, slope of regression line, integrated backscatter, or combinations of these or derived from the autoregressive model or filter coefficients or image texture based properties or others and combinations of others.

With reference again to FIG. 1, the signal properties 140 are processed by the correlation logic 145 configured to correlate the signal properties of the scan line segment with the type of vascular component having those or similar signal properties. In that regard, the correlation logic 145 is configured to compare and match the signal properties 140 to pre-determined tissue signal properties 150. In one embodiment, the pre-determined signal tissue properties 150 are configured in a data structure that associates measured or observed signal properties to a type of vascular component such as normal tissue, the lumen, and types of plaque components that may be present. Various plaque components include calcifications, fibrous tissue, lipidic tissue or foam cells, and calcified-necrotic tissue. In another embodiment, the pre-determined signal tissue properties 150 are configured in a data structure that associates measured or observed signal properties to a type of mass lesion component such as normal tissue, cancerous tissue, hyperplastic tissue, hypertrophic tissue, immune cells, and types of tumor cells that may be present. Various mass lesion components include macrophages, calcium, fibrous, fibrolipid, and necrotic regions.

The correlation logic 145 matches the signal properties 140 from a scan line, or a region of the scan line, to the pre-determined properties 150, factors in any relevant secondary parameters 160 and outputs a tissue characterization 165 that identifies the type of tissue. The system may then repeat the analysis for other segments on this scan line and for the other scan lines. In some embodiments, the system 100 may repeat the analysis for the imaging data received by each of the other imaging modalities. In some such embodiments, the system 100 utilizes the correlation logic 145 to combine the correlation conclusions from different imaging modalities to arrive at a final tissue characterization 165.

In some embodiments, as shown in FIG. 4, once a sufficient amount of ultrasound data is analyzed and characterized, the diagnostic logic 200 may be used to generate an assessment 205 as to the type and amount of plaque identified and a health condition of the patient in terms of cardiovascular disease or other associated health problems. Additionally, the diagnostic logic 200 may be configured to reconstruct the ultrasound data into displayed images and, the identified components can be visually distinguished on the display 210. Based on the assessment 205 of plaque composition, the logic 200 can be configured to generate a score indicating the health condition of a patient. For example, a score of zero may indicate no risk of heart attack while a score of ten may indicate a high risk of heart attack. With this score, a physician may recommend a particular treatment which may include monitoring, life-style changes, medication and/or surgery. The score may also be helpful to convince a patient of their condition. As mentioned above, while the example above is set forth in relation to use of an ultrasound transducer, other forms of energy emitters such lasers or light sources may be controlled to take advantage of the systems and methods described above.

Figure 8:
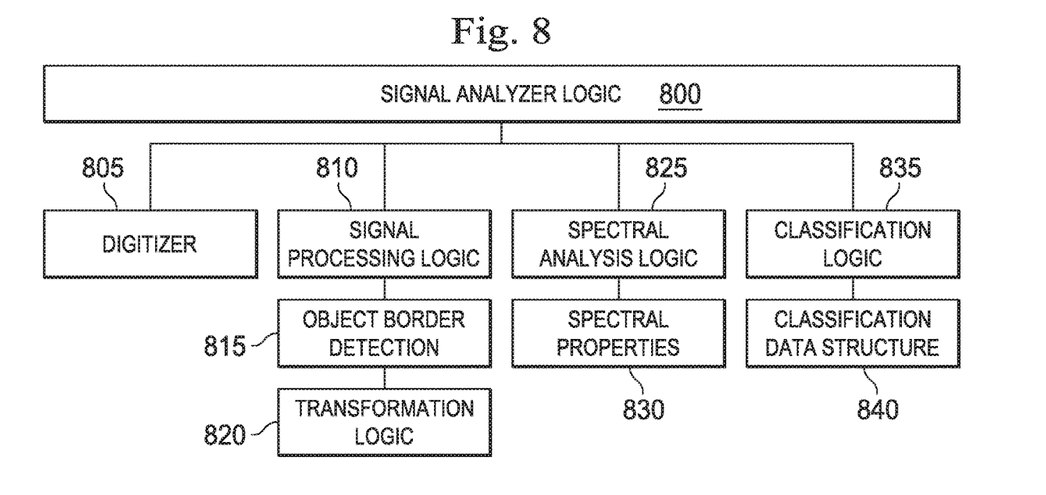
FIG. 8 is a simplified block diagram of a signal analyzer system according to one embodiment of the present disclosure.

Illustrated in FIG. 8 is one embodiment of signal analyzer logic 800 for processing and analyzing radio frequency ultrasound data. It will be appreciated that the signal analyzer logic 800 may be embodied as part of an ultrasound imaging console or as part of a separate system that receives raw radio frequency data from an ultrasound console. If the radio frequency data is in analog form, a digitizer 805 may be provided to digitize the data. A signal processing logic 810 is configured to process each scan line of the ultrasound data and transform it to a format that can be analyzed. To reduce processing time, border detection logic 815 may be used to determine the location of the borders of the vessel wall being scanned. Since the analysis is most interested in the components of the carotid artery, scan line data outside of the artery can be filtered and removed. One example of a border detection system is described in U.S. Pat. No. 6,381,350, entitled "Intravascular Ultrasonic Analysis Using Active Contour Method and System," which is incorporated herein by reference for all purposes.

After border detection, or segmentation of the tissue of interest, the scan line data is transformed. Of course, border detection can be performed after transformation. Transformation logic 820 is configured to transform the remaining scan line data into a format suitable for analysis. In general, the transformed format should match the same format used to build the pre-determined signal properties of the vascular component. In one embodiment, the transformation logic 820 transforms the data to a power spectrum plot of frequency versus power output as shown in FIG. 7. Various transformation algorithms include a Fourier transformation, Welch periodograms, and auto-regressive modeling. Other types of transformations can include transforming the data to wavelets that provide an image with frequency and time information. For example, other signal processing techniques may include wavelet decomposition or curvelet decomposition to deliver parameters that are relevant for discrimination between tissue types while not being influenced by the system transfer function of the imaging system and probe. Another transformation includes using impedance, rather than frequency, which gives an image of acoustic impedance. In this format, different tissue components have different impedance properties that provide different signal reflections. In the following example, a power spectrum density plot is used from a Fourier transformation.

With further reference to FIG. 8, spectral analysis logic 825 analyzes the power spectrum of the scan line data to determine its spectral properties 830. As mentioned previously, spectral properties or parameters may include maximum power, frequency at the maximum power, minimum power, the frequency at the minimum power, the slope, y-intercept, mid-band fit, and integrated backscatter. The spectral parameters 830 are then inputted to a classification logic 835 that attempts to classify the spectral parameters associated to a particular scan line segment with previously measured spectral parameters from a known vascular component. As mentioned above, the signal analyzing techniques need not be limited to spectral analysis and autoregressive coefficients, but could entail use of wavelet decomposition or curvelet decomposition to deliver parameters that may be used by the classification logic 835 to discriminate between tissue types.

In one embodiment, a classification data structure 840 contains a statistical classification of measured or observed spectral properties (and/or other properties) associated with particular types of vascular components. The classification data structure 840, in one embodiment, is previously generated from laboratory studies that correlate intra-vascular ultrasound data analysis of tissue samples with their corresponding histology sections. One example of this process is described in U.S. Pat. No. 6,200,268 B1, entitled "Vascular Plaque Characterization," issued Mar. 13, 2001, which is incorporated herein by reference for all purposes.

Referencing FIGS. 1 and 8, a variety of pattern recognition approaches may be used by the classification logic 835 and/or correlation logic 145. For example, the database 155 of relevant secondary parameters 160 and pre-determined tissue signal properties 150 could be the starting point of various pattern recognition approaches, covering, but not limited to, classification trees, random forests, neural networks, regression trees, principal components, and/or a combination of these, or others, to arrive at an accurate tissue characterization. For example, in one embodiment, the pre-determined tissue signal properties 150 and/or the secondary parameters 160 may be stored in the database 155 as a classification tree or a regression tree having branch node conditions based on the pre-determined tissue signal properties and one or more leaf nodes that identify a tissue component. In another embodiment, the pre-determined tissue signal properties 150 may be embodied in the database as an artificial neural network having one or more nodes that identify a tissue component. In some embodiments, the classification logic 835 and/or the correlation logic 145 may utilize a random forest classifier to analyze a number of classification trees (e.g., different classification trees based on different pre-determined signal properties or based on a multitude of different imaging modalities) to arrive at a tissue characterization.

Figure 9:
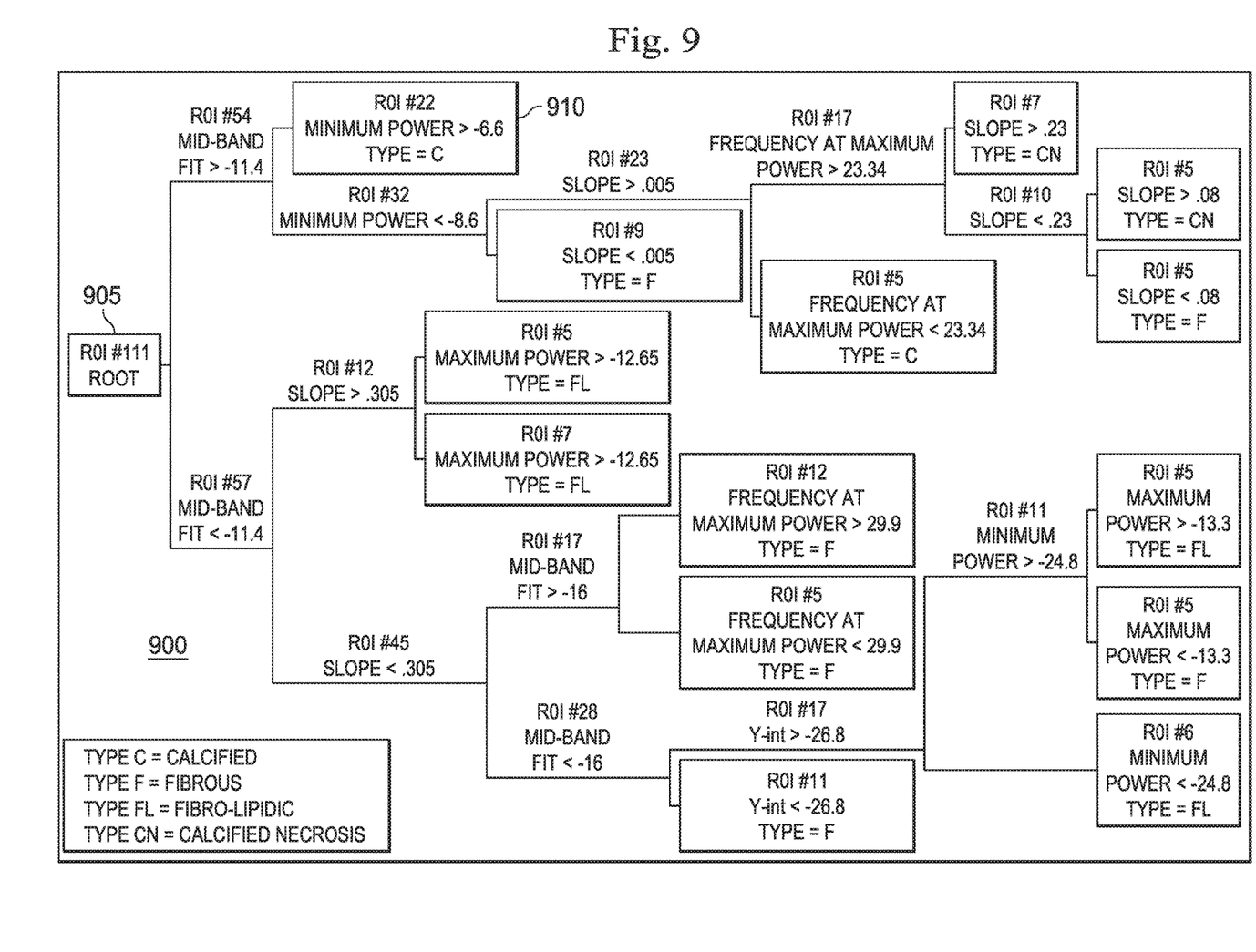
FIG. 9 is an illustration of a classification tree of spectral properties in accordance with the principles of the present disclosure.

An example of a statistical classification tree 900 is shown in FIG. 9. The tree 900 may be based on a number of spectral properties measured from ultrasound data and matched to tissue components from corresponding histology samples. A variety of statistical software applications may be used to compile the data such as S Plus by Statistical Sciences, Inc., Seattle, Wash. The tree 900 includes a root node 905 that branches based on the signal properties compiled from the statistical algorithm, and could also include other parameters relevant to patient demographics. For example, the first branch level is based on a value of mid-band fit. The tree 900 terminates at leaf nodes (shown as boxes) that represent a particular type of tissue. In this example, the leaf nodes indicate tissue type C (calcified), type F (fibrous), type FL (fibro-lipidic) and type CN (calcified necrosis). Thus, by inputting a set of signal properties, the classification tree 900 can be traversed in accordance with the branching conditions and lead to a leaf node that identifies the type of tissue matching the inputted signal properties.

In a simple example, suppose spectral properties from one segment of a backscatter signal are determined to be: mid-band fit=−11.0 and minimum power=−8.2. Processing these properties through the classification tree 900 causes the tree to be traversed in two levels and end at a leaf node 910. Reaching leaf node 910 indicates that the segment corresponds to a Type=C (calcified) plaque. In this case, other spectral properties are not necessary to identify the tissue because statistical data from the measured histology samples show that some calcified plaque tissues had a mid-band fit>−11.4 and a minimum power>−8.6 as spectral properties. Of course, these are examples of spectral properties and the values may change based on the amount and type of data collected, the statistical algorithm used, or other factors that may affect the results.

Continuing the analysis for other segments of a backscatter signal and segments from other scan lines collected from a scan, the system can provide helpful identification of the types of components within the carotid artery. Additionally, based on the location of a segment along a scan line, the system can make a determination as to the location of the corresponding tissue within the carotid artery. Then by combining data from adjacent segments and adjacent scan lines having the same tissue component, the system can estimate the size and/or volume of the tissue component. This may be important because certain components may create a greater risk of plaque rupture and/or vessel occlusion based on their location and/or size and it would be helpful to identify these conditions. Similarly, in the evaluation of other conditions, using ultrasound or other imaging modalities, certain components may indicate a greater likelihood of pathology than others.

Figure 10:
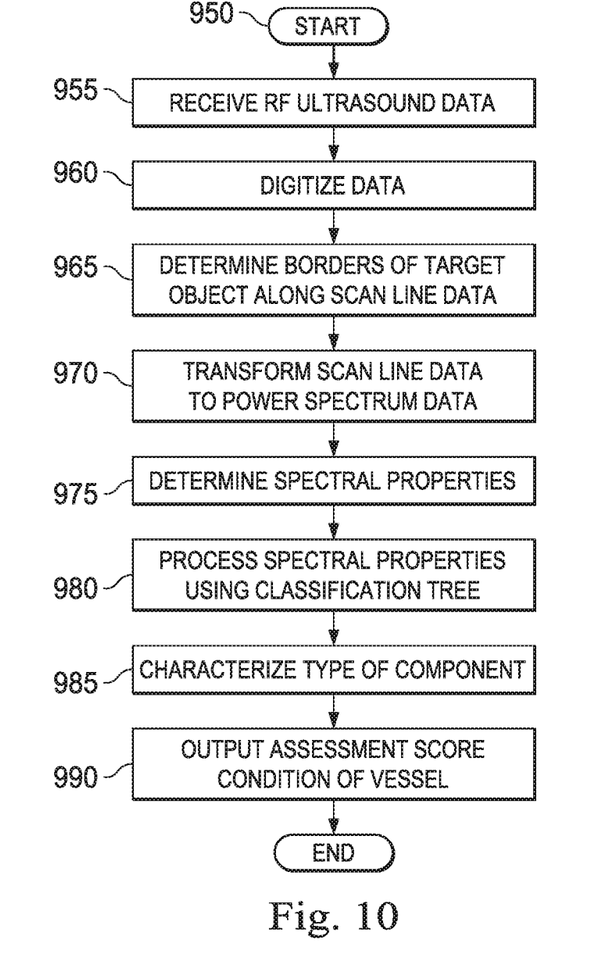
FIG. 10 is a simplified flow diagram illustrating a methodology for characterizing tissue components using the imaging system shown in FIG. 1 according to one embodiment of the present disclosure.

Illustrated in FIG. 10 is one embodiment of a methodology 950 associated with analyzing ultrasound signals and identifying the type of tissue component that corresponds to the signals. The illustrated elements denote "processing blocks" and represent computer software instructions or groups of instructions that cause a computer or processor to perform an action(s) and/or to make decisions. Alternatively, the processing blocks may represent functions and/or actions performed by functionally equivalent circuits such as a digital signal processor circuit, an application specific integrated circuit (ASIC), or other logic device. The diagram does not depict syntax of any particular programming language. Rather, the diagram illustrates functional information one skilled in the art could use to fabricate circuits, generate computer software, or use a combination of hardware and software to perform the illustrated processing. It will be appreciated that electronic and software applications may involve dynamic and flexible processes such that the illustrated blocks can be performed in other sequences different than the one shown and/or blocks may be combined or separated into multiple components. They may also be implemented using various programming approaches such as machine language, procedural, object-oriented, artificial intelligence, or other techniques. This applies to all methodologies described herein.

In other embodiments, the steps of the methodology 950 may be employed to analyze imaging signals received from another imaging modality and to identify the type of tissue component that corresponds to the signals. In such embodiments, instead of receiving ultrasound data and analyzing ultrasound imaging properties such as spectral properties, the imaging system 100 may instead receive imaging data specific to the particular type of imaging modality and analyze imaging properties specifically associated with the type of imaging modality used, in light of the relevant secondary parameters.

With reference to FIG. 10, analysis may begin as ultrasound data is received in real time during a scan or after a scan is completed (block 955). For example, in one embodiment, the region of interest for the scan is a vascular object such as a carotid artery. If the ultrasound data is still in the raw radio frequency form, it is digitized (block 960). In one embodiment, the digitized data is analyzed along a scan line, in one or more segments. The embodiment of FIG. 10 illustrates the analysis of one segment of data. Although not shown in FIG. 10, the processing repeats for each segment of a scan line and repeats for other scan lines until complete or until processing is stopped. Optionally, the process may allow for changing the properties of how a scan line is segmented such as defining various sizes and intervals of segments.

For a scan line being analyzed, a segmentation algorithm may be used to identify the borders of the target object (block 965) and the analysis can be focused on the scan line data corresponding to the target object. Since the scan is not intravascular in this example, a scan line that passes through the target object may pass through two or more walls of the object. For example, FIG. 5 illustrates a number of scan lines 520 passing through two walls of a target or scanned object 515. Thus, the border detection would attempt to search and identify at least two borders along a scan line. Many different segmentation methods are available including analyzing signal properties of the scan line, reconstructing an image from the ultrasound data and detecting borders from the image data, and other methods. Scan line data outside the borders of the target object may be ignored or removed from analysis if desired.

With reference again to FIG. 10, the scan line can be segmented and analyzed by segment. In one embodiment, the signal data from a segment is transformed to a power spectrum form (block 970) such as in FIG. 7. Spectral properties may be determined from the power spectrum (block 975) which may include the y-intercept, maximum power, mid-band fit, minimum power, frequencies at maximum and minimum powers, slope of regression line, integrated backscatter, and/or other properties from the power spectrum. Other properties may be determined from wavelet decomposition, curvelet decomposition techniques, filter coefficients, or principal component analyses. The spectral properties and/or other properties of the scan line data are then compared to corresponding pre-determined properties of known tissue components to determine which type of component best matches the scan line signal properties.

In one embodiment, the pre-determined tissue properties are structured as a classification tree generated from statistical analysis of how the properties correlate to a type of tissue component. An example of a tree structure for analysis of spectral properties is shown in FIG. 9, which includes branch nodes having conditions for spectral property values. The scan line spectral properties are then processed through the tree (block 980), traversing branches based on how the spectral properties meet the conditions of the branch nodes. The tree is traversed to a leaf node that identifies a type of tissue component. The spectral properties of the scan line segment are then characterized as this type of component (block 985).

The analysis continues for the other segments of the scan line and other scan lines. When a sufficient amount of scan line data has been characterized, an assessment can be generated and outputted reflecting a health condition of the patient and/or condition of the blood vessel (block 990). A diagnostic score and/or an image may also be generated indicating the health condition which may include a display of the imaged tissue and any associated pathology. For example, in one embodiment, the displayed image may indicate the type and amount of plaque identified, the location of the plaque, the potential risk of heart attack, or other conditions. In a situation where the user has imaged the carotid artery, by determining the condition of the carotid artery through a non-invasive scan, an assessment can be made as to a patient's cardiovascular condition. A presumption made is that there is a correlation between the condition of the carotid arteries and the condition of the coronary arteries. If the carotid arteries show certain levels of plaque, it can be presumed that similar conditions may exist in the coronaries. In another embodiment, the displayed image may indicate the type and amount of cancerous tissue identified, the location of the tumor, the potential risk of invasive cancer, or other conditions.

Other secondary factors may also be used to provide a diagnosis such as a patient's demographics, medical history, family medical history, previous treatment history, and other factors. An appropriate treatment may then be prescribed. External scanning of the patient's tissues of interest allows for a diagnosis without having to perform an invasive procedure that may expose a patient to the risks associated with biopsy and/or surgery.

In one embodiment, the system can be configured to identify tissue from an external breast scan. For example, scanning an unknown lump within a breast and determining whether it may be cancerous can serve as an early diagnostic tool. In this embodiment, pre-determined correlations between tissue signal properties and cancerous and non-cancerous tissue would be obtained and stored in the database or data structure 155 (shown in FIG. 1). The correlations can be obtained in a similar manner as those described above. This may include collecting imaging data (i.e., imaging data corresponding to a variety of different imaging modalities) from physical samples of tissue and matching the data with corresponding tissue from a histology sample of the tissue.

Such an embodiment can be implemented where the pre-determined tissue signal properties 150 within the data structure 155 would include signal properties of cancerous tissue, non-cancerous tissue, or both (as opposed to pre-determined plaque properties, for example). One form of the database 155 may be a statistical classification tree. To perform a scan, a non-invasive probe would be positioned against the tissue of a breast near a region of interest (e.g., a suspected lump). The received data (e.g., reflected imaging data) would then be analyzed to determine spectral properties or other signal properties in a similar manner as described previously. If the signal properties sufficiently match pre-determined tissue properties of cancerous tissue, the system can output a signal indicating that cancerous tissue may be present. Since the type of cancerous tissue is not as important for this type of early diagnosis, a simple YES or NO can be the output. It will be appreciated that the system can be configured to identify any desired type of tissue or object using the techniques discussed here.

Suitable software for implementing the various components of the present system and method using the teachings presented here include programming languages and tools such as Java, Pascal, C#, C++, C, CGI, Perl, SQL, APIs, SDKs, assembly, firmware, microcode, and/or other languages and tools. The components embodied as software include readable/executable instructions that cause one or more computers, processors and/or other electronic device to behave in a prescribed manner. Any software, whether an entire system or a component of a system, may be embodied as an article of manufacture and maintained as part of a computer-readable medium as defined previously. Another form of the software may include signals that transmit program code of the software to a recipient over a network or other communication medium. It will be appreciated that components described herein may be implemented as separate components or may be combined together.

The systems and methods described herein may be used in a variety of non-invasive imaging applications, including without limitation: non-invasive carotid artery and plaque imaging (resulting in characterization of plaque components as opposed to merely plaque location or thickness), non-invasive myocardium imaging, non-invasive breast cancer detection (and staging), image guidance for biopsies (i.e., needle guidance as well as for identifying cancerous versus non-cancerous tissue for biopsy tissue extraction), and non-invasive detection and/or staging of other cancers (e.g., skin cancer, oral cancer, other natural orifice cancer imaging). In some embodiments, the system shown in FIG. 1 and the method described in FIG. 10 may be used to characterize tissue to diagnose various disease states, such as, by way of non-limiting example, liver cirrhosis, kidney or gallbladder stones, ischemic myocardium, the contents of pleural effusions, bowel obstructions, joint effusions, etc. In each of these embodiments, the database 155 would be configured to contain pre-determined tissue imaging properties 150 and secondary parameters 160 associated with the particular types of tissue found in such conditions. The imaging system could utilize this database 155 to compare and correlate the signal properties of the tissue-of-interest with the pre-determined properties 150 to accurately characterize the tissue.

The systems and methods described herein provide automated, reliable, and reproducible tissue characterization using a non-invasive imaging probe and a database containing pre-determined tissue properties for various types of tissue components, thus reducing the need for highly trained, highly experienced observers and generally eliminating observer bias (as well as intra- and inter-observer variability). In addition, the systems and methods described herein may allow for a diagnosis from the tissue characterization in real-time, thereby reducing the need for tissue biopsies and the time necessary to receive a diagnosis from the biopsy results. Even in instances where a biopsy is still indicated after tissue characterization by the systems and methods disclosed herein, the systems and methods described above may be utilized to provide detailed image guidance for biopsies (i.e., directing the user to a particular tissue type or margin for biopsy). The interpretation of bi-angle or multi-angle imaging data of a target tissue offers the ability to non-invasively distinguish between anisotropic and isotropic tissues. Moreover, the systems and methods disclosed herein offer the ability to analyze multiple parameters, such as, by way of non-limiting example, a patient's pre-existing medical condition, the angles of incidence of the imaging, and/or the imaging data from multiple imaging modalities to optimize the final tissue characterization.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicant's general inventive concept.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system for determining tissue composition, the system comprising:
    an imaging system comprising a non-invasive probe with one or more active emitters, wherein the probe is configured to emit energy toward a tissue of a patient at an angle of incidence relative to a longitudinal axis of the tissue and generate imaging data based on reflections of the energy, wherein the imaging system is configured to determine the angle of incidence; and
    a processor in communication with the imaging system and configured to access a database storing a plurality of pre-determined signal property values and a plurality of corresponding angles of incidence such that each one of the plurality of pre-determined signal property values is respectively associated with one of the plurality of corresponding angles of incidence in the database, wherein the processor is further configured to:
        receive the angle of incidence from the imaging system;
        determine a signal property value based on frequency information of the imaging data, wherein the signal property value is associated with the angle of incidence;
        perform a first comparison between:
            the angle of incidence; and
            the plurality of pre-determined signal property values and the plurality of corresponding angles of incidence stored in the database;
        determine, based on the first comparison, a pre-determined signal property value stored in the database;
        classify the tissue based on a second comparison of the signal property value to the pre-determined signal property value; and
        output, to a display in communication with the processor, an indicator representing a classification of the tissue.

2. The system of claim 1, wherein the processor is configured to:
    receive an input from a user interface indicating of the angle of incidence; and
    determine the signal property value based on the indication.

3. The system of claim 1,
    wherein the probe is configured to:
        emit additional energy toward the tissue at a further angle of incidence;
        generate further imaging data based on reflections of the additional energy; and
    wherein the processor is configured to:
        determine a further signal property value based on the further imaging data, wherein the further signal property value is associated with the further angle of incidence; and
        classify the tissue based on a comparison of the further signal property value to a further pre-determined signal property value stored in the database.

4. The system of claim 3, wherein the one or more emitters are configured to emit the energy along different directions without repositioning the probe.

5. The system of claim 3, wherein the processor is configured to classify the tissue as isotropic or anisotropic.

6. The system of claim 1, wherein the processor is configured to:
    receive a selection of a secondary parameter; and
    retrieve, based on the secondary parameter, the pre-determined signal property value stored in the database, wherein the secondary parameter is associated with an imaging condition.

7. The system of claim 6, wherein the secondary parameter comprises at least one of a body mass index of the patient, a pre-existing condition of the patient, or a frequency configuration of the probe.

8. The system of claim 1, wherein the processor is configured to transform the imaging data into a frequency domain.

9. The system of claim 1, wherein the pre-determined signal property value is representative of at least one of a scatter size of the tissue, a density of the tissue, a viscosity of the tissue, an impedance of the tissue, or an attenuation of the tissue.

10. The system of claim 1, wherein the processor is configured to classify the tissue by determining a tissue type.

11. The system of claim 1, wherein the processor is configured to determine the signal property value using at least one of spectral analysis, wavelet decomposition, or curvelet decomposition.

12. The system of claim 1, wherein the probe comprises an external ultrasound imaging probe.

13. The system of claim 1, wherein the probe comprises an optical coherence tomography (OCT) probe.

14. The system of claim 1, wherein the pre-determined signal property values stored in the database are arranged by corresponding angles of incidence.

15. The system of claim 6, wherein the pre-determined signal property values stored in the database are arranged by secondary parameters.

16. The system of claim 1, further comprising the database.

* * * * *